United States Patent [19]

Maeda et al.

[11] Patent Number: 4,476,303

[45] Date of Patent: Oct. 9, 1984

[54] THIAZOLINO-[3,2-A]-1,3,5-TRIAZINE-2-ONE-4-(ONE OR THIONE) DERIVATIVES

[75] Inventors: Kuniyasu Maeda; Minoru Kaeriyama; Nobuo Matsui; Masami Mizuno; Yasushi Yasuda, all of Kanagawa; Akira Nakata, Shizuoka, all of Japan

[73] Assignee: Nippon Soda Company Limited, Tokyo, Japan

[21] Appl. No.: 467,477

[22] PCT Filed: Jun. 15, 1981

[86] PCT No.: PCT/JP81/00139

§ 371 Date: Feb. 8, 1983

§ 102(e) Date: Feb. 8, 1983

[87] PCT Pub. No.: WO82/04436

PCT Pub. Date: Dec. 23, 1982

[30] Foreign Application Priority Data

Jun. 12, 1981 [JP] Japan .................. 56-90434

[51] Int. Cl.³ .......................... C07D 513/04
[52] U.S. Cl. .................. 544/223
[58] Field of Search .......... 544/223; 425/249; 71/108

[56] References Cited

FOREIGN PATENT DOCUMENTS 5384992 11/1971 Japan .................. 544/223
508646 7/1971 Switzerland .......... 544/223

Primary Examiner—Henry R. Jiles
Assistant Examiner—J. G. Mullins
Attorney, Agent, or Firm—George B. Oujevolk

[57] ABSTRACT

Compounds having the formula

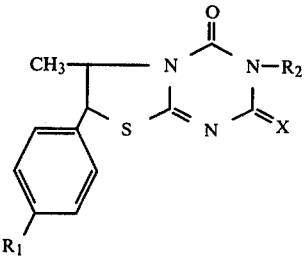

wherein
 $R_1$ denotes hydrogen atom, halogen group atom or methyl radical,
 $R_2$ denotes cyclohexyl radical, phenyl radical or phenyl radical substituted with methyl radical or nitro radical, and
 X denotes oxygen atom or sulfur atom, are useful for the control of phytophthora diseases and downy mildew of vegetable and fruit trees.

The compounds of formula [I] can be prepared by reacting compounds having the formula

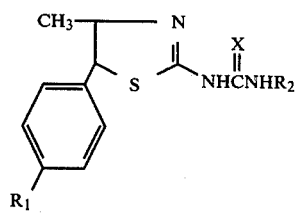

wherein $R_1$, $R_2$ and X are defined previously, are reacted with a carbonic acid derivative in the presence of an acid-binding agent.

2 Claims, No Drawings

THIAZOLINO-[3,2-A]-1,3,5-TRIAZINE-2-ONE-4-(ONE OR THIONE) DERIVATIVES

DESCRIPTION

BACKGROUND OF THE INVENTION

This invention relates to novel thiazolinotriazine derivatives, to a process for the preparation thereof, and to their use as fungicides for agriculture and horticulture.

BRIEF DESCRIPTION OF THE PROBLEM

Many agricultural fungicides used for plant diseases have been developed, however, only a few of them are effective with no phytotoxicity against control of such diseases as phytophthora diseases and downy mildew of fruit trees and vegetables. And, "chlorothalonil" (common name) is recognized as one of typical commercial products meeting the requirements.

DETAILED DESCRIPTION OF THE INVENTION

Thiazolinotriazine derivatives having the formula

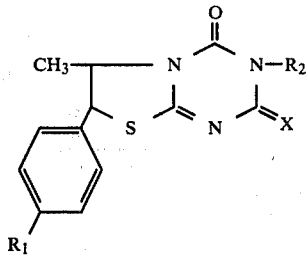

[I]

wherein
- $R_1$ denotes hydrogen atom, halogen group atom or methyl radical,
- $R_2$ denotes cyclohexyl radical, phenyl radical or phenyl radical susstituted with methyl radical or nitro radical, and
- X denotes oxygen atom or sulfur atom, are novel compounds.

The compounds of formula [I] are useful as agricultural and horticultural fungicides.

The compounds of formula [I] can be prepared by reacting compounds having the formula

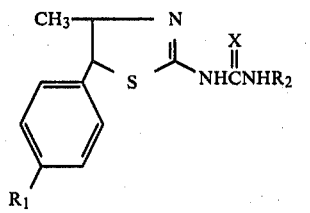

[II]

wherein $R_1$, $R_2$ and X are defined previously, are reacted with a carbonic acid derivative in the presence of an acid-binding agent.

BEST MODE OF CARRYING OUT THE INVENTION

Among the compounds of formula [I], superior fungicidal effectiveness is generally obtained for compounds having cyclohexyl radical as $R_2$. Furthermore, though the compounds of formula [I] include optical isomers, cis-form isomers usually exhibit the strongest fungicidal activity.

The compounds of formula [I] are especially useful for the control of phytophthora diseases and downy mildew of vegetable and fruit trees, and no phytotoxicity is observed when applied.

The preparation reactions are carried out in an inert organic solvent such as ethyl acetate, benzene and chloroform. The compound of formula [II] and an acid-binding agent such bases as dimethylaniline and triethylamine are dissolved in the organic solvent. A carbonic acid derivative such as potassium carbonate, phosgene, trichloromethylchloroformate, chloroformate esters and carbodiimidazole is added to the solution, and the reaction is usually continued for 1 hour to several hours at temperatures from 0° C. to boiling point of the organic solvent. After the reaction is completed, the reaction mixture is washed with water and the solvent is removed to obtain the product.

The compound of formula [II] may be prepared, for example, in accordance with following reactions,

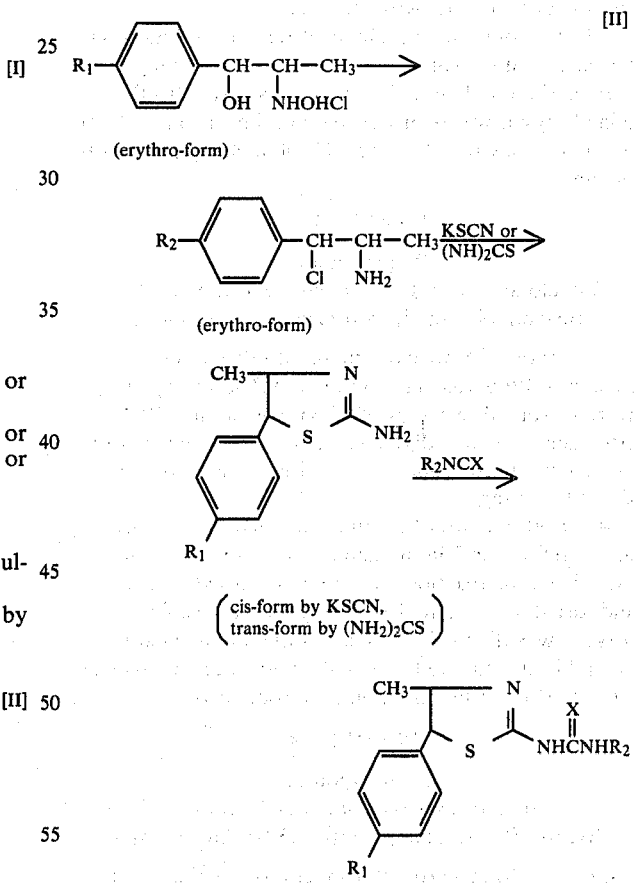

wherein $R_1$, $R_2$ and X are as defined previously.

Followings are non-limiting examples of preparing compounds of this invention.

EXAMPLE 1

Preparation of 3-cyclohexyl-6-methyl-7-phenyl-3,4-dihydro-2H-thiazolino[3,2-a]-1,3,5-triazine-2,4-dione 3.4-gr of 1-(5-phenyl-4-methyl-$\Delta^2$-thiazoline-2-yl)-3-cyclohexylurea and 2.6 gr of N,N-dimethylaniline were dissolved in 70 ml of ethyl acetate and 10 ml of ethyl acetate which dissolved 1.3 gr of trichloromethylchloroformate was added dropwise in the solution at 5° C. with stirring.

After 1 hour stirring, the reaction solution obtained was washed with water and dried over anhydrous magunesium sulfate and solvent was distilled off. Obtained residue was recrystallized from ethanol and 2.8 gr of crystal having 168°–169° C. of melting point was obtained.

EXAMPLE 2

Preparation of 3-cyclohexyl-6-methyl-7-(4-methylphenyl)-3,4-dihydro-2H-thiazolino[3,2-a]-1,3,5-triazine-2,4-dione 0.9 gr of 1-[4-methyl-5-(4-methylphenyl-$\Delta^2$-thiazolino-2-yl]-3-cyclohexylurea and 0.6 gr of N,N-dimethylaniline were dissolved in 30 ml of ethyl acetate and 10 ml of ethyl acetate which dissolved 0.4 gr of trichloromethylchloroformate was added drowise in the solution at 5° C. with stirring.

After 1 hour stirring, obtained reaction solution was washed with water and dried over anhydrous magunesium sulfate and solvent was distilled off. Obtained crystal was then washed with ligroin and 0.45 gr of crystal having 162°–165° C. of melting point was obtained.

EXAMPLE 3

Preparation of 3-cyclohexyl-6-methyl-7-phenyl-3,4-dihydro-2H-thiazolino[3,2-a]-1,3,5-triazine-2-thioxo-4-one 2.0 gr of 1-(5-phenyl-4-methy-$\Delta^2$-thiazoline-2-yl)-3-cyclohexylthiourea and 1.45 gr of N,N-dimethylaniline were dissolved in 80 ml of ethyl acetate and 10 ml of ethyl acetate which dissolved 1.2 gr of trichloromethylchloroformate was added dropwise in the solution at 5° C. with stirring.

After 30 minutes of stirring, the mixture was heated under reflux for 3 hours and cooled to room temperature. Then the reaction mixture was washed with water and dried over anhydrous magunesium sulfate, and solvent was distilled off. The residue obtained was recrystallized from methanol and 1.0 gr of crystal having 192°–193° C. of melting point was obtained.

EXAMPLE 4

Preparation of trans-7-(p-chlorophenyl)-6-methyl-2-cyclohexyl-3,4-dihydro-2H-thiazolino[3,2-a]-1,3,5-triazine-2,4-dione 4 gr of 1-[trans-5-(p-chlorophenyl)-4-$\Delta^2$-thiazoline-2-yl]-3-cyclohexylurea and 3.3 gr of N,N-dimethylaniline were dissolved in 50 ml of ethyl acetate and then 1.25 gr of trichloromethylchloroformate was added dropwise. The mixture was kept stirring at 5° C. for 30 minutes and further for 30 minutes at room temperature. Then water was added to from oil layer. Oil layer was isolated, washed with water and dried over anhydrous magunesium sulfate, and solvent was distilled off. The crystal obtained was washed with ligroin and 3.5 grs of crystal having 132°–134° C. of melting point was obtained.

EXAMPLE 5

Preparation of trans-7-(p-chlorophenyl)-6-methyl-3-cyclohexyl-3,4-dihydro-2H-thiazolino[3,2-a]-1,3,5-triazine-2,4-dione 4 gr of 1-[trans-5-(p-chlorophenyl)-4-methyl-$\Delta^2$-thiazoline-2-yl]-3-cyclohexylurea and 3.3 gr of N,N-dimethylaniline were dissolved in 50 ml of chloroform and 1.25 gr of phosgene was introduced thereto at 5° C. under stirring. The mixing was kept stirring at 5° C. for 30 minutes and further for 30 minutes at room temperature. The mixture was treated as Example 4 and 3.8 gr of crystal having 132°–134° C. of melting point was obtained.

In table 1, typical compounds of this invention are listed.

TABLE 1

Structural formula

| No. | $R_1$ | $R_2$ | X | Stereo-isomer | Melting Point [C.°] or Refractive Index |
|-----|-------|-------|---|---------------|------------------------------------------|
| 1 | H | —⟨H⟩ (cyclohexyl) | O | cis | [168–169] |
| 2 | H | —⟨H⟩ (cyclohexyl) | S | cis | [192–193] |
| 3 | H | —⟨H⟩ (cyclohexyl) | O | trans | $n_D^{31}$ 1,5928 |
| 4 | $CH_3$ | —⟨H⟩ (cyclohexyl) | O | cis | [162–165] |
| 5 | $CH_3$ | —⟨H⟩ (cyclohexyl) | O | trans | [136–138] |
| 6 | H | —⟨⟩ (phenyl) | O | cis | [183–184] |
| 7 | H | 2,6-dimethylphenyl ($CH_3$, $CH_3$) | O | cis | [180–182] |
| 8 | H | —⟨⟩-$NO_2$ | O | cis | [225–227] |
| 9 | Cl | —⟨H⟩ (cyclohexyl) | O | trans | [132–134] |
| 10 | Cl | —⟨H⟩ (cyclohexyl) | O | cis | [205–207] |

The compounds according to this invention are utilized, if desired, in a form of the usual fungicide, and various kinds of formulation, for example, wettable powder, emulsifiable concentrate and dust formulation can be applied. As additives or carriers, for solid type formulation, mineral powder such as diatom earth, apatite, talc, pyrophyllite and clay, vegetable powder such as soybean flour and wheat flour, for liquid type formulation, organic solvent such inert organic liquids as kerosene, mineral oil, petrolum, solvent naphtha, xylene, cyclohexane, cyclohexanone, dimethylfomamide, alcohol and acetate, as well as water are employed. Conventional fungicidal surface-active agent may be used when homogenous and stable formulation are desired.

Non-limiting examples of the fungicide of the invention are shown below, but additives and concentrations shall not be limited by these examples.

EXAMPLE 6

Wettable Powder

| Compound 1 | 20 parts by weight |
| Diatom earth | 73 parts by weight |
| Sodium alkylarylsulfonate | 7 parts by weight |

These components were mixed and crushed finely and wettable powder containing 20% of active ingredient was obtained.

EXAMPLE 7

Emulsible Concentrate

| Compound 2 | 20 parts by weight |
| Xylene | 42 parts by weight |
| Dimethylformamide | 30 parts by weight |
| Polyoxiethylenealkylarylether | 8 parts by weight |

These components were mixed and emulsible concentrate containing 20% of active ingredient was obtained.

EXAMPLE 8

Dust Formulation

| Compound 4 | 2 parts by weight |
| Talc | 49 parts by weight |
| Clay | 49 parts by weight |

These components were mixed and crushed and dust formulation containing 2% of active ingredient was obtained.

EXAMPLE 9

Granular Formulation

| Compound 7 | 5 parts by weight |
| Talc | 40 parts by weight |
| Clay | 39 parts by weight |
| Hentonite | 10 parts by weight |
| Sodium alkylsulfate | 6 parts by weight |

These components were mixed, finely crushed and then granulated to granular having particle size of 0.5-1.0 mm in diameter, and then granular containing 5% of active ingredient was obtained.

The wettable powder obtained and emulsifiable concentrate can be used by adding water in the forms of suspension or emulsion, and dust formulation and granular formulation can be used for prevention of plant diseases or control of plant diseases.

The fungicidal effects of compounds are illustrated by the following Tests: Test 1—Test for control of Cucumber Downy Mildew 5 ml of an aqueous supension containing desired amount of each compound was sprayed on a potted cucumber seedling (Variety: Satsukimidori) of 1.5 leaf stage and each treated cucumber was air-dried. Then Downy Mildew (*Pseudoperonospora cubensis*) was inoculated and had been kept in a greenhouse to cause the disease.

The occurrence of Cucumber Downy Mildew and phyto-toxicity were inventigated, and effect for control of the disease was evaluated in comparison with occurrence of the disease on untreated cucumber leaves.

The results are shown in Table 2.

TABLE 2

| Compound No. | Concentration of active component (ppm) | Control effect (%) | Phyto-toxicity |
|---|---|---|---|
| 1 | 400 | 100 | not observed |
|   | 200 | 100 |   |
|   | 100 | 100 |   |
|   | 50 | 100 |   |
|   | 25 | 100 |   |
| 2 | 400 | 100 | not observed |
|   | 200 | 100 |   |
|   | 100 | 100 |   |
|   | 50 | 100 |   |
|   | 25 | 100 |   |
| 3 | 400 | 100 | not observed |
| 4 | 400 | 100 | not observed |
|   | 200 | 100 |   |
|   | 100 | 100 |   |
|   | 50 | 100 |   |
|   | 25 | 100 |   |
| 5 | 400 | 100 | not observed |
| 6 | 400 | 100 | not observed |
| 7 | 400 | 100 | not observed |
| 8 | 400 | 100 | not observed |
| 9 | 400 | 100 | not observed |
|   | 200 | 100 |   |
|   | 100 | 100 |   |
|   | 50 | 100 |   |
|   | 25 | 100 |   |
| 10 | 400 | 100 | not observed |
|   | 200 | 100 |   |
|   | 100 | 100 |   |
|   | 50 | 100 |   |
|   | 25 | 100 |   |
| tetrachloroiso phthalonitrile (chlorocholonic) | 400 | 90 | not observed |
|   | 200 | 80 |   |
|   | 100 | 75 |   |
|   | 50 | 50 |   |
|   | 25 | 50 |   |

We claim:
1. A compound having the formula

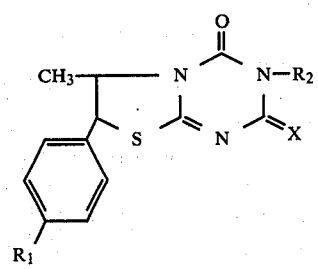
wherein
- $R_1$ denotes hydrogen atom, halogen group atom or methyl radical,
- $R_2$ denotes cyclohexyl radical, phenyl radical or phenyl radical substituted with methyl radical or nitro radical, and
- X denotes oxygen atom or sulfur atom.
2. A compound according to claim 1, wherein $R_1$ is chlorine atom, $R_2$ is cyclohexyl, and X is oxygen atom.
* * * * *